United States Patent [19]

Maurer

[11] 4,315,002
[45] Feb. 9, 1982

[54] SOLID PHARMACEUTICAL OR DIAGNOSTIC AGENT CONTAINING DEXTRAN AND ITS PREPARATION

[75] Inventor: Robert Maurer, Wattenheim, Fed. Rep. of Germany

[73] Assignee: BASF Aktiengesellschaft, Fed. Rep. of Germany

[21] Appl. No.: 154,896

[22] Filed: May 30, 1980

[30] Foreign Application Priority Data

Jun. 21, 1979 [DE] Fed. Rep. of Germany ....... 2925009

[51] Int. Cl.$^3$ ................... A61K 31/71; A61K 37/48; C12N 9/00
[52] U.S. Cl. ..................... 424/181; 424/94; 424/227; 424/271; 424/330; 435/183; 435/188; 435/191; 435/215; 435/216; 435/217; 435/219
[58] Field of Search ................ 424/94, 180, 181, 361, 424/227, 271, 330; 264/28; 435/188, 187, 183, 191, 215, 216, 217, 219

[56] References Cited

U.S. PATENT DOCUMENTS 3,655,838  4/1972  Price et al. ........................... 264/28
4,134,943  1/1979  Knitsch et al. ....................... 264/28

OTHER PUBLICATIONS

Kengo–Chem. Abst., vol. 87 (1977), p. 65,650r.
Briggs et al.–Chem. Abst., vol. 76 (1972), p. 131,492d.
Murakami et al.–Chem. Abst., vol. 83, (1975), p. 136,908y.
Okazaki et al.–Chem. Abst., vol. 87, (1977), p. 106,748m.
Okazaki et al.–Chem. Abst., vol. 86, (1977), p. 127,281y.

*Primary Examiner*—Sam Rosen
*Attorney, Agent, or Firm*—Keil & Witherspoon

[57] ABSTRACT

A process for the preparation of a solid pharmaceutical or diagnostic composition in which the active substance and dextran are dissolved in water, the solution is placed in a mold and is thereafter lyophilized to form a solid abrasion-resistant tablet which can further be compressed to reduce its rate of disintegration in water. The invention is also directed to the pharmaceutical or diagnostic agent produced by this process.

7 Claims, No Drawings

SOLID PHARMACEUTICAL OR DIAGNOSTIC AGENT CONTAINING DEXTRAN AND ITS PREPARATION

The present invention relates to a formulation of certain substances, a process for its preparation, and its use.

Substances such as pharmaceutically active compounds and sensitive materials such as enzymes, which are used as diagnostic agents, must as a rule be converted to an easily usable form. Many possible ways are known, such as tableting, production of dragees, introduction into hard gelatin capsules, etc. However, these processes as a rule consist of a plurality of stages and in many cases are unsuitable for highly sensitive substances.

It is an object of the present invention to provide a formulation of certain substances, which consists of a colyophilizate of the substance and dextran.

Another object is to provide a process for the preparation of the said formulation, wherein an aqueous solution which contains the substance and dextran is introduced into a mold and lyophilized.

A further object is to use the said formulation as a diagnostic agent in combating diseases, and to diagnostic agents or drugs which contain such formulations.

These objects are achieved by the present invention.

The formulation according to the invention does not have the conventional loose form of a lyophilizate which immediately disintegrates under pressure; rather it is, completely surprisingly, in a firm and abrasion-resistant form. The novel process therefore makes it possible even to convert highly sensitive substances, such as enzymes and proteins, into a stable solid form, which has hitherto only been possible in exceptional cases. Furthermore, this form is very abrasion-resistant.

If the formulations are not dried excessively during lyophilization, they can be compression-molded very readily without disintegrating in the process. A further advantage is that only one auxiliary, namely dextran, is necessary for the molding process.

Advantageously, the solution to be lyophilized is filled into molds having the desired shape, for example cylinders or cubes. After lyophilization, the mixture of the substance and dextran is obtained in the form of an abrasion-resistant tablet which can, if desired, be additionally compressed, whereby the rate of solution of the tablet is reduced.

The amount of the substances contained in the novel formulation can be controlled very accurately, which is particularly of importance in the case of diagnostic agents. A special advantage in this context is that even sensitive substances suffer virtually no inactivation during molding. A further advantage is that the formulation very rapidly disintegrates in water or very rapidly dissolves in water, unless it has been compressed.

Sensitive substances are substantially more stable in the novel form than in the pure state and can therefore also be stored for a prolonged period at room temperature, without loss of activity.

Examples of suitable dextrans for the novel formulation are those having molecular weights of 20,000, 40,000 and 60,000. The amount of dextran in the solution to be lyophilized should be not less than about 6%.

All substances which can be dissolved or suspended in water may be incorporated into the formulation. The formulation is particularly suitable for sensitive pharmaceutically active compounds and enzymes for diagnostic purposes and for biochemical analyses. Examples of these are antibiotics, e.g. penicillins, streptomycins and tetracyclins, and enzymes, e.g. fibrinogenase, aminoacid-oxidase, streptokinase, urokinase and caseinase. These substances may be present in the lyophilized product in an amount of from 10 to 50%.

Finally, auxiliaries, e.g. buffers, solubilizing agents or salts, may also be incorporated into the formulation, and this substantially simplifies enzymatic determinations.

The formulations absorb up to about 10% of atmospheric moisture without undergoing a change in their properties. Hence, if moisture-sensitive substances are to be kept as such formulations, the latter must be stored in the absence of atmospheric moisture.

EXAMPLE 1

Drug

2% of Verapamil are dissolved in a 10% strength solution of a dextran of molecular weight 40,000. 0.5 ml portions of the solution are lyophilized to give moldings which contain 50 mg of dextran and 10 mg of Verapamil. When left exposed to air, the moldings absorb about 6 mg of water.

EXAMPLE 2

Diagnostic agent for determination of fibrinogen 0.2 ml portions of a mixture of 10 ml of Ancrod solution (containing 70 I.U. of fibrinogenase per ml), 50 ml of a 10% strength solution of a dextran of molecular weight 40,000, which also contains 0.9% of NaCl, and 40 ml of 0.9% strength NaCl solution are lyophilized to form moldings. These each contain 1.2 I.U. of the enzyme and, when dry, weigh 12 mg.

Similar moldings are obtained if solutions of dextran of molecular weight 20,000 or 60,000 are used.

EXAMPLE 3

Diagnostic agent for determination of fibrinogen 10 ml of Ancrod solution (containing 70 I.U. of fibrinogenase per ml), 50 ml of a 10% strength solution of a dextran of molecular weight 40,000, which also contains 0.9% of NaCl, and 40 ml of buffer are mixed. 0.2 ml portions of the solution are lyophilized to give moldings.

The buffer consisted of 250 ml of an aqueous solution containing 1.838 g of sodium acetate and 7.36 g of sodium barbital, 200 ml of 4.25% strength NaCl solution, 217 ml of 0.1 N HCl and 638 ml of distilled water. The pH of the buffer had been adjusted to 7.4.

To carry out the lyophilization in Examples 1–3, the solutions were pipetted into the hollows of microtitration plates. The solutions were then frozen, and dried at −30° C. and 0.07 mbar.

We claim:

1. A process for the preparation of a solid composition containing a pharmaceutical or diagnostic agent which comprises: dissolving the pharmaceutical or diagnostic agent and dextran in water, placing the solution in a mold, and thereafter lyophilizing the solution to form a solid abrasion-resistant tablet of said agent and dextran.

2. The process of claim 1, wherein the solid abrasion-resistant tablet is compressed to reduce its rate of disintegration in water.

3. The process of claim 1 or 2, wherein the agent is an enzyme or an antibiotic.

4. The process of claim 1 or 2, wherein the agent is selected from the group consisting of pencillins, streptomycins, tetracyclins, fibrinogenase, aminoacid-oxidase, streptokinase, urokinase and caseinase.

5. The composition produced by the process of claim 1.

6. The composition produced by the process of claim 2.

7. The composition produced by the process of claim 4, wherein the agent is present in an amount from 10 to 50% by weight based on the weight of the composition.

* * * * *